United States Patent
Stock

(10) Patent No.: US 7,603,886 B2
(45) Date of Patent: Oct. 20, 2009

(54) BREATH ALCOHOL-MEASURING DEVICE WITH PIEZO DRIVE

(75) Inventor: Burkhard Stock, Luebeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 225 days.

(21) Appl. No.: 11/691,667

(22) Filed: Mar. 27, 2007

(65) Prior Publication Data

US 2007/0245801 A1    Oct. 25, 2007

(30) Foreign Application Priority Data

Apr. 25, 2006  (DE) .................... 10 2006 018 970

(51) Int. Cl.
*G01N 1/22*      (2006.01)
*G01N 31/00*     (2006.01)

(52) U.S. Cl. .............. 73/23.3; 73/23.2; 73/73.3; 180/272; 340/576; 422/84; 600/532

(58) Field of Classification Search ............. 73/23.3; 422/84; 340/576; 180/272; 600/532
See application file for complete search history.

(56) References Cited

U.S. PATENT DOCUMENTS

| | | | | |
|---|---|---|---|---|
| 4,902,628 A | * | 2/1990 | Blair | 436/132 |
| 5,739,412 A | * | 4/1998 | Stock et al. | 73/23.3 |
| 6,923,040 B2 | * | 8/2005 | Stock | 73/23.3 |
| 7,329,390 B2 | * | 2/2008 | Stock et al. | 422/84 |
| 2002/0198574 A1 | * | 12/2002 | Gumpert | 607/58 |
| 2003/0228702 A1 | * | 12/2003 | Stock et al. | 436/132 |
| 2005/0241871 A1 | * | 11/2005 | Stewart et al. | 180/272 |

FOREIGN PATENT DOCUMENTS

DE    39 04 994 A1    8/1990
DE    203 10 500 U1   10/2003

* cited by examiner

*Primary Examiner*—Hezron Williams
*Assistant Examiner*—Rachel Black
(74) *Attorney, Agent, or Firm*—McGlew and Tuttle, P.C.

(57) ABSTRACT

A breath alcohol-measuring device for breathing gas sampling has a mouthpiece (2), for receiving the exhaled breathing air (1) of a test subject, provided with a first flow diaphragm (3). A first pressure sensor (6) is connected to the mouthpiece via a first gas line upstream of the flow diaphragm (3). An alcohol sensor (4) is connected to the mouthpiece (2) via an inlet channel downstream of the flow diaphragm (3) and to a sampling system (5) for a breathing gas sample from the breathing air (1) via a second gas line. The second gas line between the alcohol sensor (4) and the sampling system (5) has a second flow restriction (diaphragm 7) and is connected to a second pressure sensor (9). An evaluating and control unit (8) receives the measured signals of the pressure sensors (6, 9) and of the alcohol sensor (4) and actuates the sampling system (5). The sampling system (5) includes a bellows (10) with a piezo drive (30) and is actuated by the evaluating and control unit (8) as a function of the volume measured by means of the second pressure sensor (9).

10 Claims, 2 Drawing Sheets

BREATH ALCOHOL-MEASURING DEVICE WITH PIEZO DRIVE

CROSS REFERENCE TO RELATED APPLICATIONS

This application claims the benefit of priority under 35 U.S.C. § 119 of German Patent Application DE 10 2006 018 970.1 filed Apr. 25, 2006, the entire contents of which are incorporated herein by reference.

FIELD OF THE INVENTION

The present invention pertains to a breath alcohol-measuring device with improved sampling. As a result, improved measuring properties can be achieved due to a variable pumping volume with preset housing dimensions of the breath alcohol-measuring device.

BACKGROUND OF THE INVENTION

A sampling system in breath alcohol-measuring devices delivers a small quantity of gas of an accurately defined volume (0.3 mL to 1 mL) from the breathing air flow into the alcohol sensor.

These systems usually comprise a piston, which is driven by a small electric motor, as described in DE 3904 994 A1, or of a bellows, which is compressed by a pushing magnet, as disclosed in DE 203 10 500 U1.

Both systems have specific drawbacks. An electric motor with a gear mechanism and a piston has limited reliability and has a low speed of response (<0.5 sec) because of the inertia of masses. A pushing magnet is relatively large and energy-intensive relative to the stroke. Also, only switching between two fixed end positions is possible with a pushing magnet. Therefore, such a pump can also only deliver a fixed volume, so that two pushing magnets are needed for the function described in DE 203 10 500 U1.

SUMMARY OF THE INVENTION

Thus, the object of the present invention is to improve a prior-art breath alcohol-measuring device in respect to sampling while maintaining or even reducing the preset overall size and the overall weight.

According to the invention, a breath alcohol-measuring device is provided with a mouthpiece for receiving the exhaled breathing air of a test subject. The mouthpiece is provided with a first flow diaphragm. A first pressure sensor is connected via a first gas line to the mouthpiece upstream of the flow diaphragm. An alcohol sensor is connected to the mouthpiece via an inlet channel downstream of the flow diaphragm and is connected to a sampling system via a second gas line for a breathing gas sample from the breathing air. The second gas line, between the alcohol sensor and the sampling system, has a second flow diaphragm and is connected to a second pressure sensor. An evaluating and control unit receives the measured signals of the pressure sensors and of the alcohol sensor and actuates the sampling system. The sampling system comprises a bellows with a piezo drive and is actuated by the evaluating and control unit depending on the volume measured by means of the second pressure sensor.

When the bellows is compressed, the piezo drive may be started by the evaluating and control unit for a breathing air sampling with breath alcohol measurement as soon as the breathing air released by the test subject reaches or exceeds a preset volume. The released volume may be measured by the evaluating and control unit by means of the pressure drop, which is measured at the first pressure sensor, that is integrated over time and is proportional to the volume flow.

The piezo drive may be stopped by means of the evaluating and control unit for the breathing air sampling as soon as the first volume measured by means of the second pressure sensor has reached a preset percentage of the maximum sampling volume. The piezo drive may be subsequently actuated for a second breathing air sampling with a second volume as soon as the pressure, which is measured at the first pressure sensor and is proportional to the volume flow, reaches or drops below a preset reference value.

The alcohol concentration measured by means of the alcohol sensor during the breath alcohol measurement may be corrected by means of a correction factor corresponding to the ratio of the measured volumes V2 and V1.

An essential advantage of the breath alcohol-measuring device according to the invention is the use of a piezo motor or piezo drive for sampling the breath alcohol sample to be measured.

This novel, piezo-based principle of actuator makes it possible to achieve long paths of displacement with linear force action and high speed of adjustment of, e.g., 300 nm per second. At the same time, the piezo drive can be stopped at any point without additional locking. The small weight of, e.g., 1.2 g. is another advantage to markedly reduce the overall weight in case of a portable breath alcohol-measuring device. The piezo motor used is a unique drive based on the piezo technology, which performs a forward and reverse motion with only one piezo ceramic.

An exemplary embodiment of the present invention will be explained below by means of the two figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
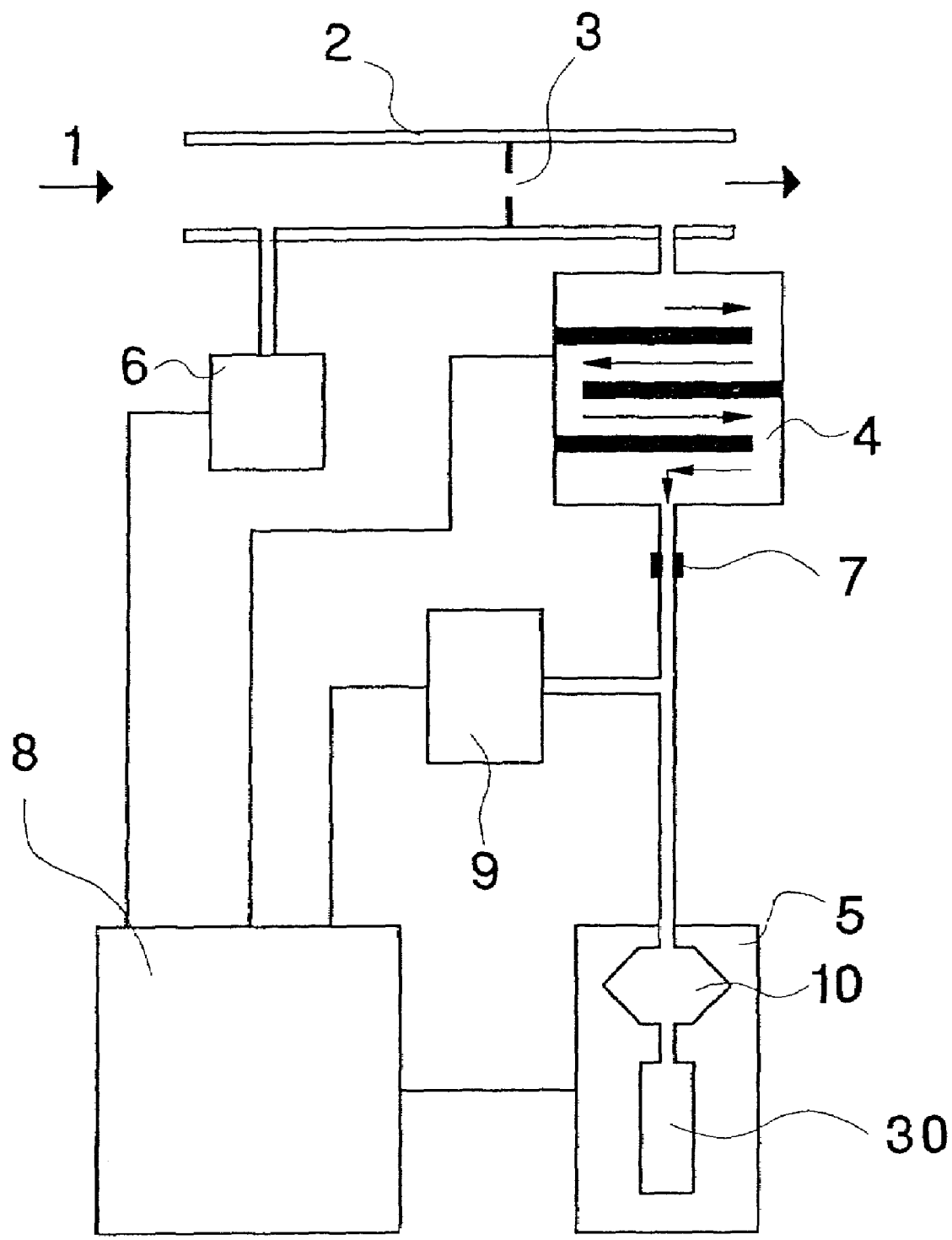
FIG. 1 is a schematic view showing a breath alcohol-measuring device according to the invention with the essential components.

Referring to the drawings in particular, the breathing air 1 or the breathing gas, represented by an arrow, which is exhaled by a test subject, flows through the generally replaceable mouthpiece 2 from the left in FIG. 1 and generates a pressure drop at a first flow diaphragm 3 that forms a first throttle (flow restriction). The mouthpiece 2 is, in general, a component of a mouthpiece holder. The mouthpiece 2 is in connection with a first pressure sensor 6. The latter measures the pressure continuously during the release of breathing air by the test subject and calculates therefrom the volume released by the test subject. When the pressure drops below a preset threshold value at the end of the expiration process, the sampling system 5 is started via the evaluating and control unit 8 and a sample is taken from the breathing air 1 into the alcohol sensor 4. It is especially important in this connection that the sample be drawn into the alcohol sensor 4 very rapidly, within preferably 20 msec, because the test subject's breath flow may also drop very rapidly, for example, within 50 msec, when the test subject suddenly removes the mouthpiece, for example, in an unforeseen manner, at the end of the expiration process. If the sampling lasts too long, the breathing air may be mixed with fresh air, and the breath alcohol concentration actually measured would be too low. A normal pumping arrangement driven by an electric motor is therefore too slow.

Sampling can be substantially accelerated by means of a piezo drive 30 as a drive element. The sampling system 5 with piezo drive 30 is explained in more detail by means of FIG. 2.

The evaluating and control unit 8 calculates the corresponding alcohol concentration from the sensor signal of the alcohol sensor 4.

The alcohol sensor 4 is preferably an electrochemical gas sensor.

Two different volumes are drawn from the breath flow into the sensor to detect the alcohol in the mouth in the process described in DE 203 10 500 U1. The first volume is drawn right at the beginning of the breath sample, the second at the end, and the first one is especially about 40% of the last one. As a result, the disturbing effect of the detection of alcohol in the mouth on the alcohol concentration measurement proper in the breathing air is considerably reduced.

When the sampling system 5 is drawing in, in the present arrangement, the air flow at the second flow diaphragm or second throttle 7 generates a pressure drop, which is measured with a second pressure sensor 9. The evaluating and control unit 8 calculates from this pressure signal a signal proportional to the volume drawn into the sensor 4.

According to DE 203 10 500 U1, two pulling magnets are necessary to embody the arrangement. Two different volumes can now be obtained with a piezo drive 30 alone. The piezo drive 30 is moved forward before the measurement, so that the bellows 10 is compressed. The piezo drive 30 is started immediately after the beginning of the breath sample, i.e., at a released breathing air volume of approximately 0.2 L. If the evaluation of the pressure signal of the second pressure sensor 9 indicates that, e.g., approximately 40% of the maximum pumping volume has been reached, the piezo drive 30 is stopped. A volume V1 is calculated from the pattern of the pressure signal measured by the second pressure sensor 9. The piezo drive 30 is again moved by the evaluating and control unit 8 into the start position about 1 second later. If the first pressure sensor 6 then signals that the breath sample is coming to an end, the piezo drive 30 is moved up to the rear end stop. The pumping volume V2 is calculated from the pressure pattern measured by the second pressure sensor 9.

To now make possible the direct comparability of the measured initial and final concentrations, the initial concentration is multiplied by the V2/V1 ratio. An extrapolation of the initial concentration with the pumping volume V1 to the pumping volume V2 of the final concentration is obtained as a result.

Since the piezo drive 30 is very lightweight, it is especially suitable for portable breath alcohol-measuring devices and especially breath alcohol-measuring devices that are used for the continuous monitoring of a test subject, especially in the case of "house arrest" applications without monitoring by the police or supervision at home or in private areas.

Based on the long path of adjustment, larger pumping volumes can be reached with a preset overall size than with the prior-art systems. As a result, the accuracy of measurement can be increased at low concentrations.

Figure 2:
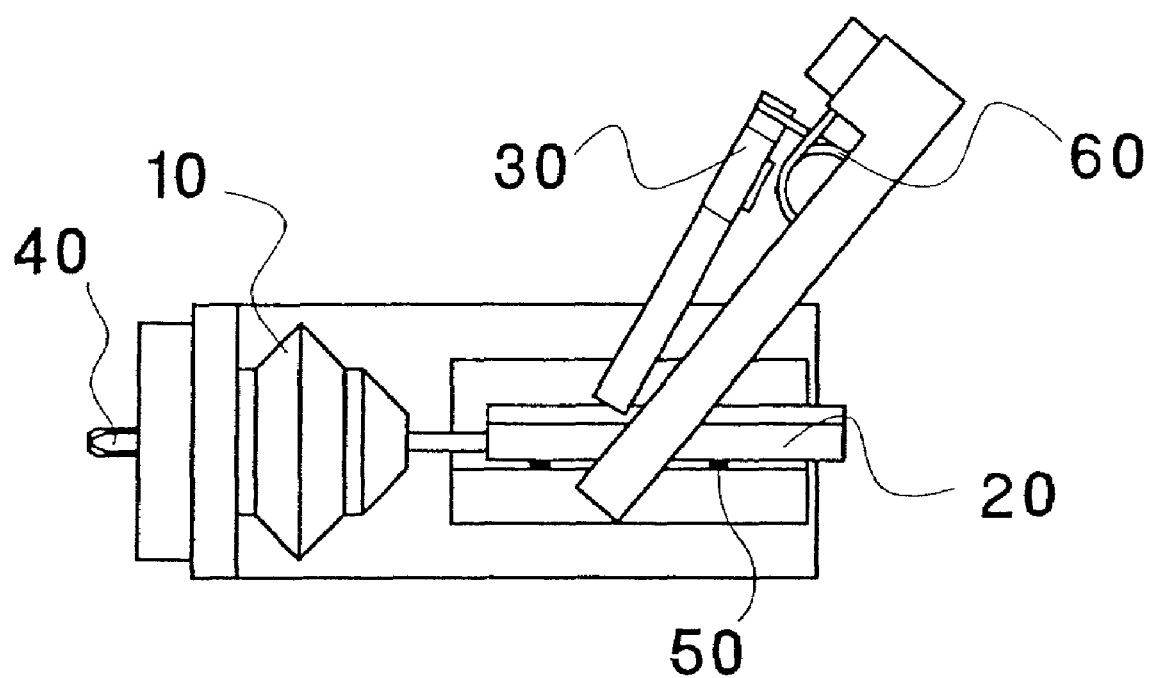
FIG. 2 a schematic view showing a sampling system of the arrangement according to FIG. 1.

FIG. 2 shows in detail the sampling system 5 from FIG. 1, which may simply be referred to as a "pump" with a piezo drive 30 as an actuator element. The sampling system 5 has a piezo drive 30 which changes length for actuation and which is pressed with a spring 60 onto a sliding carriage 20. The sliding carriage 20 runs on balls 50. The maximum range of motion is fixed by stops. The bellows 10 is compressed or pulled apart during the motion of the sliding carriage 20, and breathing air flows in or out through outlets 40.

If the electric driving current is switched off during the motion of the sliding carriage 20, the sliding carriage 20 remains fixed in the particular position due to the pressing pressure of the piezo drive 30.

While specific embodiments of the invention have been shown and described in detail to illustrate the application of the principles of the invention, it will be understood that the invention may be embodied otherwise without departing from such principles.

What is claimed is:

1. A breath alcohol-measuring device comprising:
   a mouthpiece defining a gas flow path for receiving exhaled breathing air of a test subject;
   a flow diaphragm forming a throttle in said gas flow path;
   a first gas line connected up stream of said flow diaphragm and in fluid connection with gas in said flow path;
   a first pressure sensor connected via said first gas line for detecting gas pressure in said gas flow path of said mouthpiece, upstream of said flow diaphragm;
   a second gas line;
   a sampling system comprising a bellows, in fluid connection with said second gas line, and with a piezo drive acting on said bellows to compress said bellows and to expand said bellows to draw gas into said bellows from said second gas line;
   an inlet channel connected to said mouthpiece downstream of said flow diaphragm and in fluid connection with gas in said flow path;
   an alcohol sensor connected to said mouthpiece via said inlet channel and connected to said sampling system via said second gas line for receiving a breathing gas sample from the received exhaled breathing air upon an expanding of said bellows by said piezo drive;
   a second gas line throttle providing a pressure drop in said second gas line between said alcohol sensor and said sampling system;
   a second pressure sensor connected to said second gas line between said second gas line throttle and said bellows; and
   an evaluating and control unit receiving measured signals of said first pressure sensor and said second pressure sensor and of said alcohol sensor and actuating said sampling system depending on a pressure signal of said second pressure sensor, with said pressure signal of said second pressure sensor being proportional to a gas volume drawn through said alcohol sensor.

2. A breath alcohol-measuring device in accordance with claim 1, wherein when said bellows is compressed, said piezo drive is started by said evaluating and control unit for a breathing air sampling with breath alcohol measurement as soon as said breathing air released by the test subject reaches or exceeds a preset volume, the released volume being measured by said evaluating and control unit by means of a pressure drop, which is measured at said first pressure sensor, is integrated over time and is proportional to the volume flow.

3. A breath alcohol-measuring device in accordance with claim 2, wherein said piezo drive is stopped by means of said evaluating and control unit for the breathing air sampling as soon as a first volume measured by means of said second pressure sensor has reached a preset percentage of a maximum sampling volume, and is subsequently actuated for a second breathing air sampling with a second volume as soon as the pressure, which is measured at said first pressure sensor and is proportional to the volume flow, reaches or drops below a preset reference value.

4. A breath alcohol-measuring device in accordance with claim 3, wherein alcohol concentration measured by means of said alcohol sensor during the breath alcohol measurement is corrected by means of a correction factor corresponding to the ratio of the first volume to the second volume.

5. A breath alcohol-measuring device comprising:
   a mouthpiece with an inlet and an outlet, the mouthpiece receiving exhaled breathing air of a test subject and defining a flow path for flow of the received exhaled breathing air;
   a flow restriction in said flow path;
   a first gas line connected to said flow path upstream of said flow restriction and in fluid connection with gas in said flow path;
   a first pressure sensor connected to said flow path via said first gas line;
   a second gas line;
   a sampling system comprising a bellows in fluid connection with said second gas line, and with a piezo drive acting on said bellows to compress said bellows and to expand said bellows to draw gas into said bellows from said second gas line;
   an inlet channel connected to said flow path downstream of said flow restriction and in fluid connection with gas in said flow path;
   an alcohol sensor connected to said flow path via said inlet channel and connected to said sampling system via said second gas line for receiving a breathing gas sample from the exhaled breathing air flow upon an expanding of said bellows by said piezo drive;
   a second gas line throttle providing a pressure drop in said second gas line between said alcohol sensor and said sampling system;
   a second pressure sensor connected to said second gas line between said second gas line throttle and said; and
   an evaluating and control unit receiving measured signals of said first pressure sensor and said second pressure sensor and of said alcohol sensor and actuating said sampling system depending on a pressure signal, proportional to a volume drawn into said alcohol sensor, measured by means of said second pressure sensor.

6. A breath alcohol-measuring device in accordance with claim 5, wherein when said bellows is compressed, said piezo drive is started by said evaluating and control unit for a breathing air sampling with breath alcohol measurement as soon as said breathing air released by the test subject reaches or exceeds a preset volume, the released volume being measured by said evaluating and control unit by means of a pressure drop, which is measured at said first pressure sensor, is integrated over time and is proportional to the volume flow.

7. A breath alcohol-measuring device in accordance with claim 6, wherein said piezo drive is stopped by means of said evaluating and control unit for the breathing air sampling as soon as a first volume measured by means of said second pressure sensor has reached a preset percentage of a maximum sampling volume, and is subsequently actuated for a second breathing air sampling with a second volume as soon as the pressure, which is measured at said first pressure sensor and is proportional to the volume flow, reaches or drops below a preset reference value.

8. A breath alcohol-measuring device in accordance with claim 7, wherein alcohol concentration measured by means of said alcohol sensor during the breath alcohol measurement is corrected by means of a correction factor corresponding to the ratio of the first volume to the second volume.

9. A breath alcohol-measuring device comprising:
   a mouthpiece with a mouthpiece inlet and a mouthpiece outlet, the mouthpiece receiving exhaled breathing air of a test subject and defining a gas flow path for flow of the received exhaled breathing air;
   a flow restriction in said flow path;
   a first gas line connected to said flow path upstream of said flow restriction and in fluid connection with gas in said flow path;
   a first pressure sensor connected to said flow path via said first gas line for detecting gas pressure in said gas flow path upstream of said flow restriction in said flow path;
   a second gas line;
   an inlet channel connected to said flow path downstream of said flow restriction and in fluid connection with gas in said flow path;
   an alcohol sensor connected to said flow path via said inlet channel and connected to said second gas line;
   a sampling system comprising a bellows in fluid connection with said second gas line, and with a piezo drive acting on said bellows to compress said bellows to force gas out of said bellows into said second gas line and to expand said bellows to draw gas into said bellows from said second gas line so as to draw received exhaled breathing air into said alcohol sensor via said inlet channel;
   a second gas line throttle providing a pressure drop in said second gas line between said alcohol sensor and said sampling system;
   a second pressure sensor connected to said second gas line between said second gas line throttle and said bellows for sensing pressure in said second gas line between said second gas line throttle and said bellows for sensing the expanding of said bellows and to provide a pressure signal proportional to a gas volume drawn into said alcohol sensor;
   an evaluating and control unit receiving measured signals of said first pressure sensor and said second pressure sensor and of said alcohol sensor and actuating said sampling system including:
   with said bellows compressed, starting said piezo drive to draw breathing air released by the test subject through said alcohol sensor by drawing gas into said bellows, upon said first pressure sensor providing a pressure signal, which integrated over time, indicates a volume of exhaled breathing air flow of received exhaled breathing air;
   subsequent to said starting, stopping said piezo drive upon said second pressure sensor providing a pressure signal, which integrated over time, indicates a preset percentage of a maximum sampling volume has been reached providing a first sampling volume;
   subsequent to said stopping, again starting said piezo drive for a second breathing air sampling with a second volume, upon said first pressure sensor providing a pressure signal, which reaches or drops below a preset reference value; and subsequent to said again starting, again stopping said piezo drive upon said second pressure sensor providing a pressure signal, which integrated over time, indicates a preset percentage of a maximum sampling volume has been reached providing a second sampling volume.

10. A breath alcohol-measuring device in accordance with claim 9, wherein alcohol concentration measured by means of said alcohol sensor during the breath alcohol measurement is corrected by means of a correction factor corresponding to the ratio of the first sampling volume to the second sampling volume.

* * * * *